(12) United States Patent
Kim et al.

(10) Patent No.: US 9,034,916 B2
(45) Date of Patent: May 19, 2015

(54) **PHARMACEUTICAL COMPOSITION FOR THE PREVENTION OR TREATMENT OF A NEURODEGENERATIVE DISEASE, COMPRISING A *DAPHNE GENKWA* EXTRACT OR A COMPOUND ISOLATED THEREFROM**

(75) Inventors: Won Gon Kim, Daejeon (KR); Baek Soo Han, Daejeon (KR); Kyoung Shim Kim, Daejeon (KR); Kwang Soo Kim, Daejeon (KR); Young Mi Kang, Daejeon (KR); Yu Jin Kim, Daejeon (KR); Chun Hyung Kim, Lexington, MA (US); Mi Jin Sohn, Daejeon (KR); Hoe Yune Jung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/009,526

(22) PCT Filed: Nov. 28, 2011

(86) PCT No.: PCT/KR2011/009110
§ 371 (c)(1),
(2), (4) Date: Jan. 28, 2014

(87) PCT Pub. No.: WO2012/138034
PCT Pub. Date: Oct. 11, 2012

(65) Prior Publication Data
US 2014/0142173 A1 May 22, 2014

(30) Foreign Application Priority Data

Apr. 6, 2011 (KR) .................. 10-2011-0031614
Nov. 24, 2011 (KR) .................. 10-2011-0123848

(51) Int. Cl.
| | | |
|---|---|---|
| *A01N 43/02* | (2006.01) | |
| *A61K 31/335* | (2006.01) | |
| *A01N 43/08* | (2006.01) | |
| *A61K 31/34* | (2006.01) | |
| *A01N 37/00* | (2006.01) | |
| *A61K 31/21* | (2006.01) | |
| *A01N 31/14* | (2006.01) | |
| *A61K 31/075* | (2006.01) | |
| *A01N 31/00* | (2006.01) | |
| *A61K 31/045* | (2006.01) | |
| *A61K 31/357* | (2006.01) | |
| *A61K 36/83* | (2006.01) | |

(52) U.S. Cl.
CPC .............. *A61K 31/357* (2013.01); *A61K 36/83* (2013.01)

(58) Field of Classification Search
USPC ................ 514/463, 449, 461, 506, 715, 724
See application file for complete search history.

(56) References Cited

FOREIGN PATENT DOCUMENTS

| KR | 10-2001-0081188 A | 8/2001 |
|---|---|---|
| KR | 10-2004-0012396 A | 2/2004 |
| KR | 10-2004-0013675 A | 2/2004 |
| KR | 10-2004-0029072 A | 4/2004 |
| KR | 10-2006-0028076 A | 3/2006 |
| KR | 10-2009-0084130 A | 8/2009 |
| KR | 10-2010-0060123 A | 6/2010 |
| KR | 10-2010-0060949 A | 6/2010 |
| KR | 10-2011-0013466 A | 2/2011 |

OTHER PUBLICATIONS

International Search Report and Written Opinion, PCT/KR2011/009110, Korean Intellectual Property Office, Jul. 7, 2012.
Kai et al., "Pharmacological Effects of *Daphne genkwa* and Chinese Medicine Presecription, "Jyu-So-Tu"," Yakugaku Zasshi, 124(6):349-354, 2004.
Hong et al., "Evaluation of natural products on inhibition of inducible cyclooxygenase (COX-2) and nitric oxide synthase (iNOS) in cultured mouse macrophage cells", Journal of Ethnopharmacology, 83 (Jul. 17, 2002) 153-159.
Notice of Allowance, Korean Patent Application No. 9-5-2014-050280455, Korean Intellectual Property Office, Jul. 24, 2014.
Shixuan Zhang et al., "Evaluation of *Daphne genkwa* Diterpenes: Fingerprint and Quantitative Analysis by High Performance Liquid Chromatography", A Phytochemical Analysis, vol. 18 , pp. 91-97 , 2007.
Xu, W.-C. et al., "Phytochemical and Biological Studies of the Plants from the Genus *Daphne*", Chem. & Biodiversity, 2011, 8: 1215-1233.
Chu, Y. et al., "Nurr1 in Parkinson's Disease and Related Disorders", J. Comp. Neurol., 2006, 494(3): 495-514.
Kyoungho Suk, "Monoamine Oxidase Inhibitory Activity by Natural Products", Research focus on natural producs and the body's immune and inflammatory systems. New York: Nova Biomadical Books. 2007, pp. 44-47.

*Primary Examiner* — Yong Chong
(74) *Attorney, Agent, or Firm* — Joseph R. Baker, Jr.; Gavrilovich, Dodd & Lindsey LLP (57) ABSTRACT

The present invention relates to: a pharmaceutical composition or a Nurr1 activating composition for the prevention or treatment of a neurodegenerative disease or a disease induced by impaired Nurr1 function, wherein the composition comprises an active ingredient in the form of genkwanin N or yuanhuacine, a *Daphne genkwa* extract comprising one or more of the above compounds, or a fraction thereof; or a functional food additive for preventing or alleviating a neurodegenerative disease or a disease induced by impaired Nurr1 function, wherein the additive comprises genkwanin N or yuanhuacine, a *Daphne genkwa* extract comprising one or more of the above compounds, or a fraction thereof; and a method for the prevention or treatment of a neurodegenerative disease or a disease induced by impaired Nurr1 function, wherein the method comprises the step of administering the pharmaceutical composition.

6 Claims, 3 Drawing Sheets

```
SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: GAL4 gene

<400> SEQUENCE: 1
ctcggaggac agtactccg                                                    19
```

PHARMACEUTICAL COMPOSITION FOR THE PREVENTION OR TREATMENT OF A NEURODEGENERATIVE DISEASE, COMPRISING A *DAPHNE GENKWA* EXTRACT OR A COMPOUND ISOLATED THEREFROM

This application is a U.S. National Stage Application filed under 35 U.S.C. §371 and claims priority to International Application No. PCT/KR2011/009110, filed Nov. 28, 2011, which application claims priority under 35 U.S.C. §119 to Korean Application No. 10-2011-0031614, filed Apr. 6, 2011, and Korean Application No. 10-2011-0123848, filed Nov. 24, 2011, the disclosures of which are incorporated herein by reference.

TECHNICAL FIELD

The present invention relates to a pharmaceutical composition for preventing or treating neurodegenerative disease or a disease that is caused by Nurr1 dysfunction, or a composition for activating Nurr1, the composition comprising, as an active ingredient, a genkwanine N or yuanhuacine compound, or a *Daphne genkwa* extract or a fraction thereof, which comprises one or more of the compounds, and to a functional food additive for preventing or ameliorating neurodegenerative disease or a disease that is caused by Nurr1 dysfunction, the functional food additive comprising, as an active ingredient, a genkwanine N or yuanhuacine compound, or a *Daphne genkwa* extract or a fraction thereof, which comprises one or more of the compounds, and also to a method for preventing or treating neurodegenerative disease or a disease that is caused by Nurr1 dysfunction, the method comprising administering the pharmaceutical composition.

BACKGROUND ART

Neurodegenerative diseases are associated with conditions in which neurons degenerate, lose their function, and often die. Because these diseases are generally progressive, the consequences of neurodegenerative diseases are often very devastating. Patients with neurodegenerative disease may undergo severe deterioration in cognitive or motor skills. As a result, the quality of life and life expectancy of the patients may be considerably reduced. In humans, these diseases include Parkinson's disease (PD), Alzheimer's disease (AD), amyotrophic lateral sclerosis (ALS), Huntington's disease (HD), fronto-temporal dementia, cortico basal degeneration, progressive supranuclear palsy (PSP), and other diseases.

Meanwhile, it is known that Nurr1 (nuclear receptor-related 1) protein is implicated in a considerable number of neurodegenerative diseases. The term "Nurr1" refers to nuclear receptor-related 1 protein, also known as NR4A2 (nuclear receptor subfamily 4, group A, member 2). The Nurr1 protein is known to be encoded by the human NR4A2 gene. Although the Nurr1 protein is an orphan nuclear receptor whose ligand has not yet been clearly identified, it was identified that the Nurr1 protein is a member of the nuclear receptor family of intracellular transcription factors, which plays a key role in maintaining the dopaminergic system in the brain. It is known that, when abnormalities in the Nurr1 or NR4A2 gene occur, the function of the dopaminergic system is damaged to cause Parkinson's disease and a wide range of inflammatory and neuropathic diseases, including rheumatoid arthritis, schizophrenia and manic depression.

Parkinson's disease, a typical neurodegenerative disease that is caused by Nurr1 dysfunction, is a chronic progressive neurodegenerative disease that affects brain neurons that control muscle movement. It occurs when cells that produce the neurotransmitter dopamine in substantia nigra are damaged suddenly or degenerated or the number thereof greatly decreases. Because dopamine is an important chemical that is involved in intracellular signaling for facilitating body movement, motor syndromes, including tremor, rigidity, bradykinesia, postural instability and akinesia, typically occur in the case of Parkinson's disease. Although the cause of damage to the dopamine-producing cells has not yet been clearly identified, cerebral arteriosclerosis, carbon monoxide poisoning, it is known that damage to these cells is related to cerebral arteriosclerosis, carbon-monoxide poisoning, medication, metabolic or traumatic encephalitis sequelae induced by hypoparathyroidism, etc.

Known drugs for treating Parkinson's disease include L-dopa drugs, dopamine receptor agonists, anti-cholinergic drugs, Eldepryl (or depreyl), etc. Most of these drugs do not provide causal treatment of Parkinson's disease, but act to control conditions, and thus need to be administered continually. However, the long-term administration of such drugs causes side effects. For example, anti-cholinergic drugs may cause autonomic nervous system abnormalities or abnormal mental functions, and for this reason, continuous administration thereof to aged patients is limited. In addition, in the case of L-dopa drugs, the long-term administration thereof leads to a gradual decrease in the effect and causes side effects, including abnormal movements such as body twisting, or spontaneous movement of the hands or feet.

In order to prevent such side effects, efforts have been actively made to develop natural material-derived agents for treating Parkinson's disease. For example, Korean Patent Laid-Open Publication No. 2001-0081188 discloses a composition for preventing and treating brain diseases and neural diseases, including Parkinson's disease and senile dementia, the composition comprising, as an active ingredient, a *Scutellariae* radix extract having the effect of protecting neurons. Korean Patent Laid-Open Publication No. 2004-0012396 discloses a composition for treating neurodegenerative diseases such as Parkinson's disease and paralysis, the composition comprising an extract of *Beauveria bassiana* 101A. Korean Patent Laid-Open Publication No. 2004-0029072 discloses a pharmaceutical composition for treating Parkinson's disease, which comprises an extract obtained from the bark of *Wenguanguo*. Korean Patent Laid-Open Publication No. 2010-0060123 discloses a pharmaceutical composition for preventing or treating Parkinson's disease, which comprises a ginger extract or shogaol. Korean Patent Laid-Open Publication No. 2010-0060949 discloses a neuron-protecting composition for preventing or treating diseases such as Parkinson's disease, which comprises a peach leaf extract as an active ingredient. Korean Patent Laid-Open Publication No. 2011-0013466 discloses a pharmaceutical composition for treating Parkinson's disease, which comprises, as an active ingredient, a grape seed extract or one or more compounds derived therefrom. These components derived from natural materials have no side effects, but have a shortcoming in that the efficiency of treatment of Parkinson's disease is low.

DISCLOSURE

Technical Problem

The present inventors have found that an extract derived from the stem and root of *Daphne genkwa* that is a natural material has no side effects and activates Nurr1 to enhance the differentiation, growth and survival of dopaminergic neuronal cells, thereby exhibiting an excellent therapeutic effect against a variety of neurodegenerative diseases, including Parkinson's disease, which are caused by Nurr1 dysfunction. In addition, the present inventors have analyzed the active ingredients of the Daphne genkwa extract, and as a result, have found that the genkwanine N and yuanhuacine compounds of the extract have an excellent effect on the activation of Nurr1 protein, thereby completing the present invention.

Technical Solution

It is an object of the present invention to provide a pharmaceutical composition for preventing or treating neurodegenerative disease, the composition comprising, as an active ingredient, one or more terpenoid compounds selected from the group consisting of a genkwanine N represented by formula 1 and a yuanhuacine represented by formula 2, a pharmaceutically acceptable salt thereof, or a Daphne genkwa extract or a fraction thereof, which comprises one or more of the compounds.

Another object of the present invention is to provide a pharmaceutical composition for preventing or treating a disease that is caused by Nurr1 dysfunction, the composition comprising, as an active ingredient, a Daphne genkwa extract, a fraction thereof or a compound represented by formula 1 or 2.

Still another object of the present invention is to provide a composition for activating Nurr1, the composition comprising, as an active ingredient, a Daphne genkwa extract, a fraction thereof or a compound represented by formula 1 or 2.

Still another object of the present invention is to provide a functional food additive for preventing or ameliorating neurodegenerative disease, the functional food additive comprising, as an active ingredient, one or more terpenoid compounds selected from the group consisting of a genkwanine N represented by formula 1 and a yuanhuacine represented by formula 2, a pharmaceutically acceptable salt thereof, or a Daphne genkwa extract or a fraction thereof, which comprises one or more of the compounds.

Still another object of the present invention is to provide a method for preventing or treating neurodegenerative disease, the method comprising administering a pharmaceutical composition comprising, as an active ingredient, one or more terpenoid compounds selected from the group consisting of a genkwanine N represented by formula 1 and a yuanhuacine represented by formula 2, a pharmaceutically acceptable salt thereof, or a Daphne genkwa extract or a fraction thereof, which comprises one or more of the compounds.

Yet another object of the present invention is to provide a method for preventing or treating a disease that is caused by Nurr1 dysfunction, the method comprising administering a pharmaceutical composition comprising, as an active ingredient, a Daphne genkwa extract, a fraction thereof or a compound represented by formula 1 or 2.

Advantageous Effects

A Daphne genkwa extract of the present invention or a compound isolated therefrom is derived from a natural material and exhibits an excellent effect of restoring Nurr1 protein activity, inhibited by neuronal damage, without causing any side effects. Thus, it can be used to prevent or treat neurodegenerative diseases, including Parkinson's disease, which are caused by the inhibition of activity of Nurr1 protein.

BEST MODE

To achieve the above objects, in one aspect, the present invention provides a pharmaceutical composition for preventing or treating neurodegenerative disease, the composition comprising, as an active ingredient, one or more terpenoid compounds selected from the group consisting of a genkwanine N represented by the following formula 1 and a yuanhuacine represented by the following formula 2, a pharmaceutically acceptable salt thereof, or a Daphne genkwa extract or a fraction thereof, which comprises one or more of the compounds:

Formula 1

Formula 2

The genkwanine N of the present invention is a terpenoid compound represented by formula 1, particularly a diterpene ester compound, and can be prepared according to a method known to those skilled in the art. For example, it can be isolated and purified from plants known to contain genkwanine N using a polar or non-polar solvent. In addition, it is commercially available or can be prepared by synthesis. Preferably, it can be extracted and isolated from *Daphne genkwa*.

The yuanhuacine of the present invention is a terpenoid compound represented by formula 2, particularly a diterpene ester compound, and can be prepared according to a method known to those skilled in the art. For example, it can be isolated and purified from plants known to contain yuanhuacine using a polar or non-polar solvent. In addition, it is commercially available or can be prepared by synthesis. Preferably, it can be extracted and isolated from *Daphne genkwa*.

As used herein, the term "*Daphne genkwa*" refers to a dicotyledonous deciduous shrub belonging to the family Elaeagnaceae of the order Myrtales. It grows mainly on the seashore. In Chinese medicine, it is used to treat disorders such as difficult urination, dropsy and nephritis.

As used herein, the term "*Daphne genkwa* extract" refers to an extract obtained from *Daphne genkwa*, preferably an extract obtained from the stem or root of *Daphne genkwa*, more preferably an extract obtained by extracting the stem or root of *Daphne genkwa* with an organic extract, and even more preferably an extract obtained by extracting the stem or root of *Daphne genkwa* with a $C_1$-$C_5$ lower alkyl alcohol. As is known in the art, the *Daphne genkwa* extract generally contains coumarins, flavonoids, lignans, terpenoids and five other major compounds, and the total number of compounds contained in the *Daphne genkwa* extract reaches several hundred kinds [Xu, W.-C. et al., *Chem. Biodiversity*, 2011, 8: 1215-1233].

In an example of the present invention, the ground dry stem and/or root of *Daphne genkwa* was soaked in an about 2-20-fold volume (preferably about 3-5-fold volume) of a solvent such as water or an organic solvent, for example, a $C_1$-$C_5$ lower alkyl alcohol (e.g., methanol, ethanol, butanol, etc.) for 3-5 hours and filtered to separate it into a solid component and a first liquid component, and the solid component was soaked in the same manner as described above and was filtered to obtain a second liquid component which was then mixed with the first liquid component. Then, the mixture was concentrated under reduced pressure, and the residue was freeze-dried, thereby obtaining a *Daphne genkwa* extract. The *Daphne genkwa* extract can contain the genkwanine N or yuanhuacine compound.

In another example of the present invention, the obtained *Daphne genkwa* extract was fractionated using solvents such as distilled water or mixed organic solvents, for example, hexane, ethyl acetate and butanol, and the solvent fractions were collected separately, and a high purity of an active ingredient was isolated and purified from each of the fractions using a purification method known in the art, such as chromatography. The hexane fraction of the *Daphne genkwa* extract can contain the genkwanine N or yuanhuacine compound of the present invention.

Figure 1:
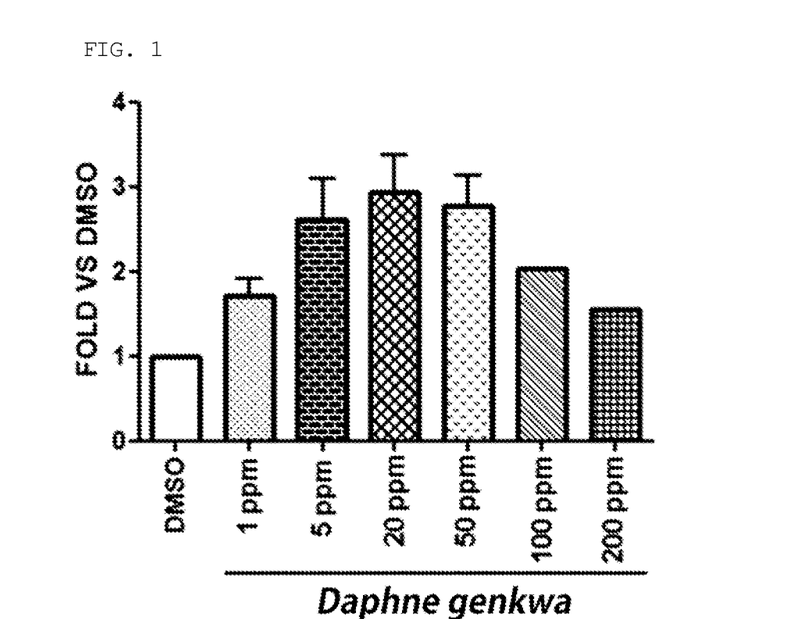
FIG. 1 is a graphic diagram showing the results of a luciferase assay conducted to examine the change in Nurr1 protein activity as a function of the concentration of a Daphne genkwa extract.

The present inventors have conducted studies on various types of extracts obtained from various natural materials in order to find natural material-derived components that have an excellent effect of preventing or treating various diseases, including Parkinson's disease, which are induced by Nurr1 dysfunction, and at the same time, have no side effects. As a result, the present inventors have found that an organic solvent extract of *Daphne genkwa* can Nurr1 activity (FIG. 1).

Figure 2:
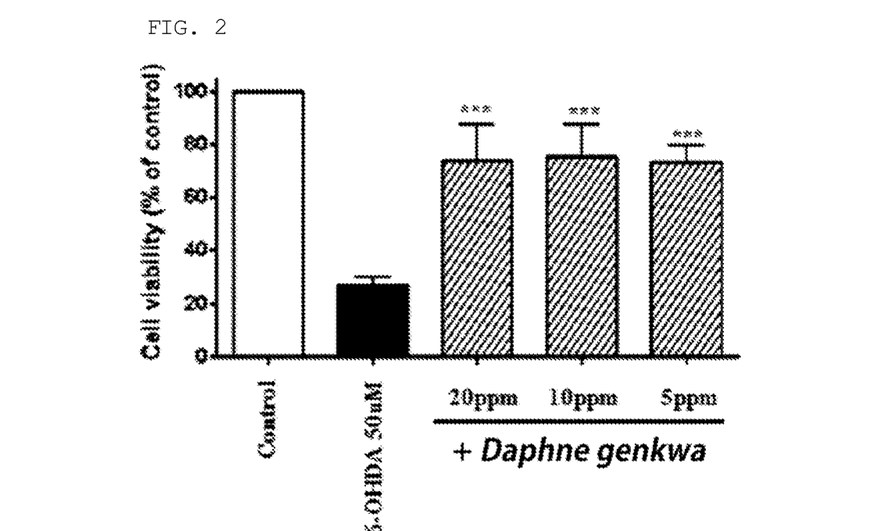
FIG. 2 is a graphic diagram showing the effects of varying concentrations of a Daphne genkwa extract against neuronal cell death that is induced by 6-OHDA (6-hydroxydopamine).
Figure 3:
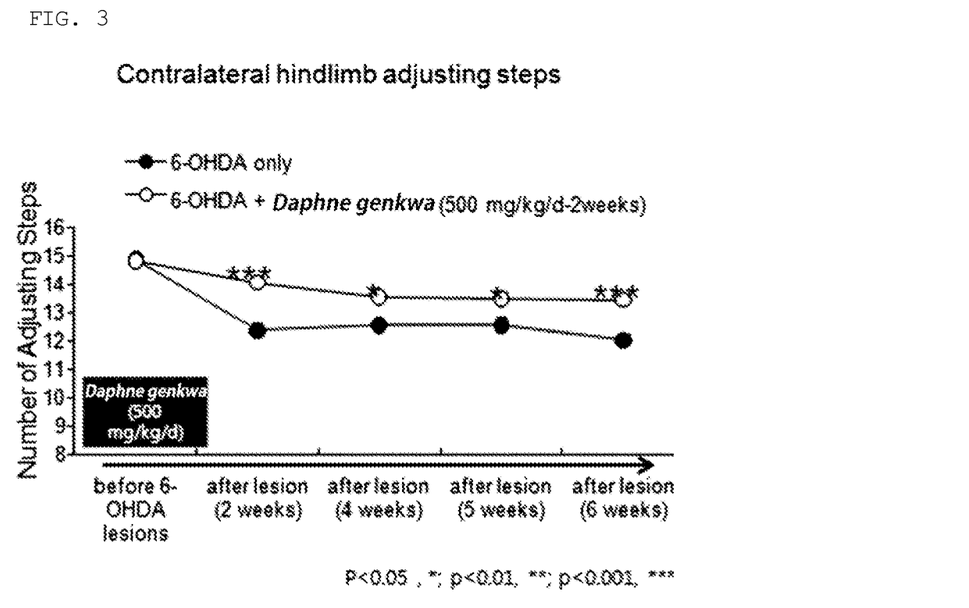
FIG. 3 is a graphic diagram showing the therapeutic effect of a Daphne genkwa extract in a Parkinson's disease animal model.

Moreover, the present inventors have found that the *Daphne genkwa* extract that increases Nurr1 activity exhibits the effect of preventing neuronal cell damage from being caused by compounds (e.g., 6-OHDA, etc.) known to induce neuronal cell death (FIG. 2). In addition, it could be seen that, when an animal model obtained by killing the dopaminergic neuronal cells of the brain of a rat was fed with a mixture of feed with the *Daphne genkwa* extract, the neural function damaged by the killed dopaminergic neuronal cells was slowly improved (FIG. 3).

Thus, the present inventors have found that the *Daphne genkwa* extract shows the effect of increasing Nurr1 protein activity, thereby exhibiting the effect of preventing or treating various diseases, for example, Parkinson's disease, which are caused by damage to dopaminergic neuronal cells that are affected directly by the activity of Nurr1 protein, and various diseases that are caused by Nurr1 dysfunction.

Figure 4:
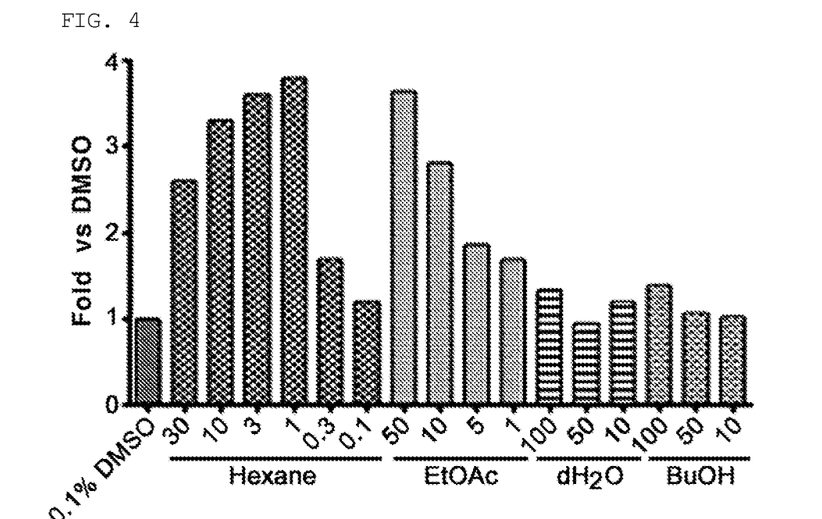
FIG. 4 is a graphic diagram showing the changes in Nurr1 protein activity caused by various solvent extracts of Daphne genkwa.
Figure 5:
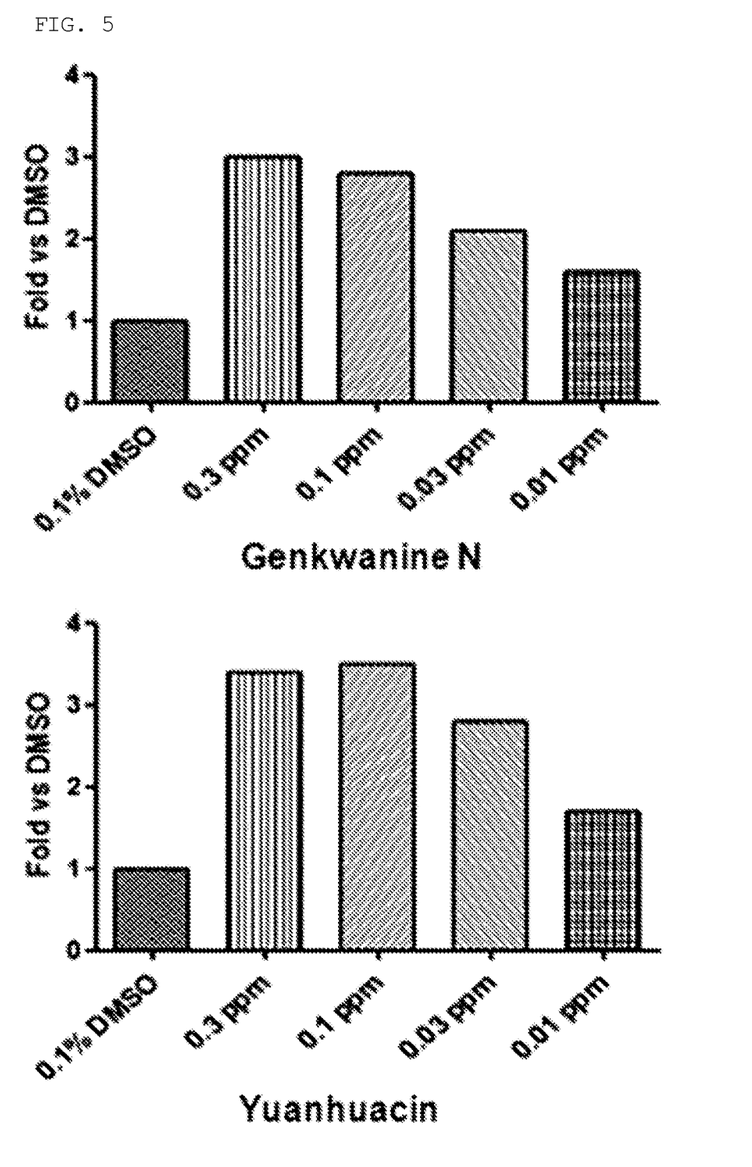
FIG. 5 is a graphic diagram showing the increase in Nurr1 protein activity as a function of the concentrations of the genkwanine N and yuanhuacine compounds isolated from a Daphne genkwa extract.

The present inventors have analyzed the active fractions and active ingredients of the *Daphne genkwa* extract, which activate the Nurr1 protein, and as a result, have found that the hexane or ethyl acetate fraction of the *Daphne genkwa* extract shows an effect of activating the Nurr1 protein (FIG. 4) and that the genkwanine N and yuanhuacine compounds of the extract show an excellent effect of activating the Nurr1 protein (FIG. 5). It was found that the Nurr1 protein is involved in the establishment and maintenance of the dopaminergic phenotype of a specific cell group in the central nervous system and that a decrease in the expression of Nurr1 is involved in neurodegenerative diseases, including Parkinson's disease [Chu, Y. et al., *J. Comp. Neurol.*, 2006, 494(3): 495-514]. Thus, it can be seen that the hexane or acetate fraction and genkwanine N or yuanhuacine compound of the *Daphne genkwa* extract can show the effect of increasing Nurr1 protein activity, thereby exhibiting the effect of preventing or treating various diseases, for example, Parkinson's disease, which are caused by damage to dopaminergic neuronal cells that are affected directly by the activity of Nurr1 protein, and various diseases that are caused by Nurr1 dysfunction.

Thus, the genkwanine N and yuanhuacine compounds of the present invention, which have the effect of activating Nurr1, can be effectively used for the prevention or treatment of neurodegenerative diseases, including Parkinson's disease. As used herein, the term "neurodegenerative diseases" refers to diseases associated with conditions in which neurons degenerate, lose their function, and often die. Because these diseases are generally progressive, the consequences of neurodegenerative diseases are often very devastating, and patients with neurodegenerative disease may undergo severe deterioration in cognitive or motor skills. The neurodegenerative diseases include, but are not limited to, Parkinson's disease (PD), Alzheimer's disease (AD), amyotrophic lateral sclerosis (ALS), Huntington's disease (HD), fronto-temporal dementia, cortico basal degeneration, and progressive supranuclear palsy (PSP).

The pharmaceutical composition of the present invention may contain the genkwanine N of formula 1, the yuanhuacine of formula 2, or a pharmaceutically acceptable salt thereof. As used herein, the term "pharmaceutically acceptable salt" refers to any salts that retain the desired biological and/or physiological activity of the above compound and exhibit minimal undesired toxicological effects. For the salts, acid-addition salt formed by a pharmaceutically acceptable free acid thereof is useful and can be prepared by a conventional method. For example, it is prepared by dissolving the compound in an excess amount of acid solution and precipitating the salt by a water-miscible organic solvent such as methanol, ethanol, acetone or acetonitrile. A mixture of an equivalent molar amount of the compound and acid or alcohol (e.g., glycol monomethylether) in water can be heated, and then the mixture can be dried by evaporation, or the precipitated salt can be filtrated by suction. As the free acid, inorganic acid or organic acid can be used. Examples of the inorganic acid include, but are not limited to, hydrochloric acid, hydrobromic acid, phosphoric acid, nitric acid, sulfuric acid, tartaric acid and the like, and examples of the organic acid include, but are not limited to, methansulfonic acid, p-toluensulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid and the like.

Further, a pharmaceutically acceptable metal salt of the compound may be prepared using a base. The alkali metal or alkali-earth metal salt of the compound can be prepared, for example, by dissolving the compound in an excess amount of an alkali metal hydroxide or alkali-earth metal hydroxide solution, filtering the insoluble salt, and then evaporating and drying the filtrate. As the metal salt, a sodium, potassium or calcium salt is pharmaceutically suitable, but is not limited thereto. In addition, the corresponding silver salt can be prepared by reacting alkali metal salt or alkali-earth metal salt with suitable silver salt such as silver nitrate.

The pharmaceutically acceptable salts of the genkwanine N compound of formula 1 or the yuanhuacine compound of formula 2 include salts of acidic or basic groups that may be present in the genkwanine N or yuanhuacine compound, unless otherwise indicated. Examples of the pharmaceutically acceptable salt include sodium, calcium and potassium salts of a hydroxyl group, and other pharmaceutically acceptable salts of an amino group include hydrobromide sulfate, hydrosulfate, phosphate, hydrophosphate, dihydrophosphate, acetate, succinate, citrate, tartarate, lactate, mandelate, methanesulfonate (mesylate) and, p-toluenesulfonate (tosylate) salts. These salts can be prepared by a method known in the art.

In another aspect, the present invention provides a pharmaceutical composition for preventing or treating neurodegenerative disease, the composition comprising, as an active ingredient, the genkwanine N or yuanhuacine compound, a pharmaceutically acceptable salt thereof, or a *Daphne genkwa* extract or a fraction thereof, which comprises one or more of the compounds, together with a pharmaceutically acceptable carrier.

As used herein, the term "pharmaceutically acceptable carrier" refers to a carrier or diluent that does not cause irritation to an organism and does not abrogate the biological activity and properties of the administered compound. When the composition is formulated into a liquid solution, the pharmaceutically acceptable carrier may be one or more of saline, sterile water, Ringer's solution, buffered saline, albumin injection solution, dextrose solution, maltodextrin solution and glycerol, which are sterile and biocompatible. If necessary, other conventional additives, including an antioxidant, a buffer and a bacteriostatic agent, may be added to the composition.

In still another aspect, the present invention provides a pharmaceutical composition for preventing or treating a disease that is caused by Nurr1 dysfunction, the composition comprising, as an active ingredient, the *Daphne genkwa* extract, a fraction thereof or the compound represented by formula 1 or 2.

As used herein, the term "Nurr1 (nuclear receptor related 1)" refers to nuclear receptor-related 1 protein, also known as NR4A2 (nuclear receptor subfamily 4, group A, member 2). The Nurr1 protein is known to be encoded by the human NR4A2 gene. Moreover, it is known that Nurr1 is involved in a considerable number of neurodegenerative diseases. Although the Nurr1 protein is an orphan nuclear receptor whose ligand has not yet been clearly identified, it was identified that the Nurr1 protein is a member of the nuclear receptor family of intracellular transcription factors, which plays a key role in maintaining the dopaminergic system in the brain. Examples of the disease that is caused by Nurr1 dysfunction include, but are not limited to, neurodegenerative diseases such as Parkinson's disease (PD), Alzheimer's disease (AD), amyotrophic lateral sclerosis (ALS), Huntington's disease (HD), fronto-temporal dementia, cortico basal degeneration and progressive supranuclear palsy (PSP), as well as a wide range of inflammatory diseases, including rheumatoid arthritis, schizophrenia and manic depression, which are caused by dopaminergic dysfunction.

In still another aspect, the present invention provides a composition for activating Nurr1, the composition comprising, as an active ingredient, the *Daphne genkwa* extract, a fraction thereof or the compound represented by formula 1 or 2.

Although the Nurr1 protein in the present invention is an orphan nuclear receptor whose ligand has not yet been clearly identified, it was identified that the Nurr1 protein is a member of the nuclear receptor family of intracellular transcription factors, which plays a key role in maintaining the dopaminergic system in the brain. In addition, it is known that abnormalities in the Nurr1 protein may cause damage to the dopaminergic system and result in neurodegenerative diseases, and thus Nurr1 has been studied as a target for neurodegenerative disease-related proteins. Thus, the genkwanine N or yuanhuacine compound of the present invention can be used for studies on the function of Nurr1, but is not limited thereto.

In still another aspect, the present invention provides a functional food additive for preventing or alleviating neurodegenerative disease, the composition comprising, as an active ingredient, one or more terpenoid compounds selected from the group consisting of a genkwanine N represented by formula 1 and a yuanhuacine represented by formula 2, or a *Daphne genkwa* extract or a fraction thereof, which comprises one or more of the compounds.

The composition of the present invention contains *Daphne genkwa* extract, which is a natural material, or a compound isolated therefrom, and thus has verified safety. Thus, when the composition of the present invention is usually eaten according to usual eating habits for a long period of time, it can exhibit the effects of preventing Parkinson's disease and ameliorating the conditions of Parkinson's disease developed.

As used herein, the term "preventing" refers to all actions that inhibit or delay the development of neurodegenerative disease by activating Nurr1 protein using the composition comprising, as an active ingredient, one or more terpenoid compounds selected from the group consisting of a genkwanine N represented by formula 1 and a yuanhuacine represented by formula 2, or a *Daphne genkwa* extract or a fraction thereof, which comprises one or more of the compounds.

As used herein, the term "ameliorating" refers to all actions that reduce symptoms of neurodegenerative disease in a subject suspected of having or known to have neurodegenerative disease, by activating Nurr1 protein using the composition comprising, as an active ingredient, one or more terpenoid compounds selected from the group consisting of a genkwanine N represented by formula 1 and a yuanhuacine represented by formula 2, or a *Daphne genkwa* extract or a fraction thereof, which comprises one or more of the compounds.

When the genkwanine N compound of formula 1, the yuanhuacine of formula 2, or the *Daphne genkwa* extract or a fraction thereof, which comprises one or more of the compounds, is used as a food additive, it may be added alone to fools or beverages or used in combination with other food additives. When the food additive of the present invention is added in the preparation of a food or a beverage, it may be added in an amount of 1-5 wt %, preferably 1-3 wt %, based on the weight of the final food, but is not specifically limited thereto. However, when the food additive is taken for the purpose of health and hygiene or health control for a long period of time, it may be used in an amount smaller than the lower limit of the above range. Further, the active ingredient may also be used in an amount larger than the upper limit of the above range, because it is not problematic in terms of safety.

In addition, the above food or beverage is meant to include all foods or beverages in a general sense. Preferred examples of the above food or beverage include, but are not limited to, meats, sausages, bread, chocolate, candies, snack, confectionery, pizza, noodles, gum, dairy products including ice cream, various soups, beverages, teas, drinks, alcoholic beverages and multi-vitamin preparations.

When the food additive comprising the compound isolated from the *Daphne genkwa* extract of the present invention is added to a food, it may be added together with various auxiliary components, including nutrients, vitamins, electrolytes, flavoring agents, colorants, pectic acid and its salt, alginic acid and its salt, organic acids, protective colloidal thickeners, pH adjusting agents, stabilizers, preservatives, glycerin, alcohols, and the like. The content of the auxiliary components is not specifically limited, but is preferably 0.01-0.1 wt % based on the weight of the final food.

In addition, when the food additive comprising the compound isolated from the *Daphne genkwa* extract of the present invention is added to a beverage, the beverage may additionally contain various sweetening agents or natural carbohydrates, which are contained in conventional beverages. Herein, examples of the sweeteners include, but are not limited to, natural sweeteners such as thaumatin and stevia extracts, and synthetic sweeteners such as saccharin and aspartame. Examples of the natural carbohydrates include, but are not limited to, monosaccharides (e.g., glucose, fructose, etc.), disaccharides (e.g., maltose, sucrose, etc.), polysaccharides (e.g., dextrin, cyclodextrin, etc.), and sugar alcohols (e.g., xylitol, sorbitol, erythritol, etc.). The content of the natural carbohydrates is not specifically limited, but is preferably about 0.01-0.04 g, and more preferably about 0.02-0.03 g, based on 100 ml of the final beverage.

In still another aspect, the present invention provides a method for preventing or treating neurodegenerative disease, the method comprising administering to a subject in need thereof a pharmaceutical composition comprising, as an active ingredient, a terpenoid compounds selected from the group consisting of a genkwanine N represented by formula 1 and a yuanhuacine represented by formula 2, a pharmaceutically acceptable salt thereof, or a *Daphne genkwa* extract or a fraction thereof, which comprises one or more of the compounds.

In still another aspect, the present invention provides a method for preventing or treating a disease that is caused by Nurr1 dysfunction, the method comprising administering to a subject in need thereof a pharmaceutical composition comprising, as an active ingredient, the *Daphne genkwa* extract, a fraction thereof, or the compound represented by formula 1 or 2.

The present invention also provides the use of a pharmaceutical composition, which comprises, as an active ingredient, the *Daphne genkwa* extract, a fraction thereof, or the compound represented by formula 1 or 2, for preparation of a medicament for treating a disease that is caused by Nurr1 dysfunction.

As used herein, the term "subject" refers to all animals, including humans, who have or are at risk of developing neurodegenerative disease. The neurodegenerative disease or the disease that is caused by Nurr1 dysfunction can be effectively prevented or treated by administering the pharmaceutical composition of the present invention to a subject. Moreover, the pharmaceutical composition of the present invention may be administered alone or in combination with other therapeutic agents, and may be administered sequentially or simultaneously with conventional therapeutic agents.

As used herein, the term "administering" refers to introducing a specific substance into a patient by an appropriate method. The composition may be administered by any general route, as long as it can reach a target tissue. In addition, the composition may be administered intraperitoneally, intravenously, intramuscularly, subcutaneously, intradermally, orally, topically, intranasally, intrapulmonarily or intrarectally, but is not limited thereto. Solid formulations for oral administration include tablets, pills, powders, granules, capsules, etc. These solid formulations may be prepared by mixing at least one compound with one or more excipients, for example, starch, calcium carbonate, sucrose, lactose, gelatin, etc. In addition to simple excipients, lubricants such as magnesium stearate and talc may be used. In addition, liquid formulations for oral administration include suspensions, solutions, emulsions and syrups, etc. In addition to water commonly used as a simple diluent and liquid paraffin, various excipients, for example, wetting agents, sweetening agents, flavors, preservatives, etc. may be included. However, when the composition is administered orally, the *Daphne genkwa* extract derived from a natural material can be lost due to digestion in the stomach, and for this reason, the oral composition should be formulated so that the active ingredient is coated or protected from decomposition in the stomach. Formulations for parenteral administration include sterile aqueous solutions, non-aqueous solutions, suspensions, emulsions, freeze-dried formulations, suppositories, etc. Propylene glycol, polyethylene glycol, vegetable oils such as olive oil, injectable esters such as ethyl oleate, etc. may be used as non-aqueous solvents and suspending agents. Suppositories may include witepsol, macrogol, tween 61, cacao butter, laurin butter, glycerinated gelatin, etc.

In addition, the pharmaceutical composition of the present invention may be administered using any system capable of delivering the active ingredient to target cells. Preferred administration modes and formulations are intravenous injection, subcutaneous injection, intracutaneous injection, intramuscular injection, instillation or the like. Injectable formulations may be prepared using saline, aqueous solutions such as Ringer's solution, and non-aqueous solutions, such as vegetable oils, high fatty acid esters (e.g., ethyl oleic acid, etc.), alcohols (e.g., ethanol, benzylalcohol, propylene glycol, glycerin, etc.). The injectable preparations may comprises pharmaceutical carriers, including a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

The composition may be administered in a pharmaceutically effective amount in a single or multiple dosage form. As used herein, the term "pharmaceutically effective amount" refers to an amount sufficient to treat diseases, at a reasonable benefit/risk ratio applicable to any medical treatment. The effective dosage level of the composition may be determined depending on the severity of the disease, the activity of the drug, the patient's age, weight, physical condition and sex, the patient's sensitivity to the drug, the time of administration of the inventive composition used, the route of administration of the composition, the excretion rate, the duration of treatment, drugs combined or used in combination with the composition, and other factors well known in the medical field.

MODE FOR INVENTION

Hereinafter, the present invention will be described in further detail with reference to examples. It is to be understood, however, that these examples are for illustrative purposes only and are not intended to limit the scope of the present invention.

Example 1

Preparation of *Daphne genkwa* Extract 1,260.93 g of the stem of *Daphne genkwa* and 1,487.17 g of the root of *Daphne genkwa* were cut finely, immersed in 13 l of methanol for 4 hours, and filtered to separate it into a solid component and a first liquid component. The separated solid component was immersed in 13 l of methanol for 4 hours, and filtered to obtain a second liquid component. The obtained first liquid component and second liquid component were mixed with each other, and the mixture was concentrated under reduced pressure. The residue was freeze-dried, thereby obtaining 172.71 g of a *Daphne genkwa* extract.

Example 2

Isolation of Active Ingredient from *Daphne genkwa* Extract by Various Solvents

To the extract obtained in Example 1 by extracting the root and stem of *Daphne genkwa* with methanol, concentrating the extracted material under reduced pressure and drying the concentrate, various solvents were sequentially added. The effect of each of the solvent fractions on Nurr1 protein activity was analyzed. The solvents used were hexane, ethyl acetate (EtOAc), distilled water ($dH_2O$), and butanol (BuOH).

Specifically, the dry *Daphne genkwa* extract was dissolved and fractionated in 2 L of a 1:1 mixed solvent of distilled water and hexane, and the hexane layer was collected. The remaining distilled water layer was added to and fractionated in 2 L of a 1:1 mixed solvent of distilled water and ethyl acetate, and the ethyl acetate layer was collected. In the same manner as described above, the butanol layer and the distilled water layer were obtained. Each of the fractions of the collected solvent fractions was subjected to a Nurr1 activity test, and as a result, it was shown that the hexane and ethyl acetate fractions had high Nurr1 activities. In order to isolate large amounts of the active fractions, according to a method similar to the method described in Example 1, 2.75 kg of the dry root and stem of *Daphne genkwa* were repeatedly macerated twice in 13 L of methanol solvent for each marceration, followed by concentration, thereby obtaining 172.71 g of a methanol extract. 30.1 g of the extract was suspended in distilled water and fractionated sequentially with hexane and ethyl acetate. Among the two fractions, the hexane fraction (3 g) determined to have higher activity was eluted by silica gel column chromatography with a gradient of hexane and ethyl acetate (10:1, 5:1, 2:1, 1:1, 1:2, 1:5, and 1:10), thereby obtaining a total of 50 fractions. Among these fractions, fractions 32 to 38 (268 mg) eluted with a gradient of hexane:ethyl acetate of 1:2 showed Nurr1 activity. Thus, fractions 32 to 38 were collected together and subjected to reverse phase silica gel prep TLC using 85% acetonitrile as an eluent, thereby obtaining a total of 11 bands. Among the bands, band 6 (Rf=0.44) and band 8 (Rf=0.33) showed Nurr1 activity. Thus, active ingredients were extracted from the two bands with methanol and extracted under reduced pressure, thereby obtaining two compounds B6 and B8. Finally, ODS HPLC was performed using 80% acetonitrile (0.025% trifluoroacetic acid (TFA)) as an eluent, thereby successfully isolating two active ingredients (genkwanine N and yuanhuacine) as single substances with a purity of 99% or higher.

Example 3

Effect of *Daphne genkwa* Extract on Nurr1 Protein Activity

A gene comprising eight repeats of a nucleotide sequence (5'-CTCGGAGGACAGTACTCCG-3, SEQ ID NO: 1) to which GLA4 gene can bind was linked to the reporter gene luciferase to synthesize a vector. Then, three kinds of plasmid DNAs, including a DNA comprising Nurr1-LBD and a DNA having β-galactosidase, were transfected into BE(2)C cells, and after 6 hours, the cells were treated with 1-200 ppm of the *Daphne genkwa* extract. The treated cells were incubated in a 5% $CO_2$ incubator at 37° C. for 20 hours, and then subjected to a luciferase assay (FIG. 1).

FIG. 1 is a graphic diagram showing the results of a luciferase assay conducted to examine the change in Nurr1 protein activity as a function of the concentration of the *Daphne genkwa* extract. As a control, 0.1% DMSO was used, and the increase in activity was expressed as folds of the activity of the control. When the cells were treated with 20 ppm of the *Daphne genkwa* extract, the highest activity was shown and was about 3 folds of the control. As can be seen in FIG. 1, the activity of Nurr1 protein in the BE(2)C cells that are human neuroblasts was increased by the *Daphne genkwa* extract.

Example 4

Effect of *Daphne genkwa* Extract on SH-SY5Y Cells

Human neuroblastoma SH-SY5Y cells were seeded into a 24-well plate at a density of $5 \times 10^5$ cells/well and cultured in a $CO_2$ incubator for 24 hours. The cultured cells were treated with 50 μM of 6-OHDA (6-hydroxydopamine) as cell death inducer alone or together with different concentrations (5 to 20 ppm) of the *Daphne genkwa* extract and incubated in a 5% $CO_2$ incubator at 37° C. for 24 hours. After 24 hours, each well of the plate was treated with 1 mg/ml of MIT (3-(4,5-dimethylthiazol-2-yl)-2,5-diphenyltetrazolium bromide) solution and incubated in a 5% $CO_2$ incubator for 1 hour, and then MTT extraction solution was added thereto. Then, the plate was incubated at 37° C. for 24 hours, and the absorbance of each well at 570 nm was measured (FIG. 2).

FIG. 2 is a graphic diagram showing the effects of different concentrations of the *Daphne genkwa* extract against neuronal cell death that is induced by 6-OHDA. As can be seen in FIG. 2, neuronal cell death that is induced by 6-OHDA was inhibited by the *Daphne genkwa* extract, and the cell viability of the group treated with the *Daphne genkwa* extract was restored to 70% or higher of the control group.

Example 5

Effect of *Daphne genkwa* Extract on Rats with Damaged Neurons

To specifically kill the dopaminergic neuronal cells present in the substantia nigra of a 6-week-old SD rat (Core Tech Co., Ltd.), 4 μg of 6-OHDA (1 μg/μl) was injected directly into the AP (−4.3), ML (−1.8) and DV (−8.2) site and AP (−5.0), ML (−1.8) and DV (−8.2) site of the cerebral hemisphere at a rate of 1 μl/min using a stereotaxic tool. At 30 minutes before the administration of 6-OHDA, desipramine was administered to the rat at a dose of 25 mg/kg to inhibit the death of cells other than the dopaminergic neuronal cells.

Next, the rat was fed with a feed containing the *Daphne genkwa* extract for 2 weeks in such a manner that the daily dose of the *Daphne genkwa* extract was 500 mg/kg. In a control group, a rat fed with a feed containing no *Daphne genkwa* extract was used.

A stepping test that is a non-pharmacological test method having reduced error compared to a pharmacological test method was carried out. Specifically, in a state in which three limbs of the rat were controlled by hand, the rat was allowed to move on a 90 cm-long table for 15 seconds while the number of steps of the uncontrolled limb on the table surface was repeatedly measured three times for each limb. The number of steps was measured at 3 days for injection of 6-OHDA and 2 weeks, 4 weeks, 5 weeks and 6 weeks after injection of 6-OHDA (FIG. 3).

FIG. 3 is a graphic diagram showing the results of the stepping test conducted to measure the effect of the *Daphne genkwa* extract on the rat with killed dopaminergic neurons. As can be seen in FIG. 3, the number of steps of the rat fed with the *Daphne genkwa* extract increased compared to that of the rat fed with no *Daphne genkwa* extract.

Example 6

Effects of Various Solvent Fractions of *Daphne genkwa* Extract

The effects of the *Daphne genkwa* extract fractions, obtained using various solvents in Example 2, on Nurr1 protein activity, were analyzed according to a method similar to the method described in Example 3. The solvents used were hexane, ethyl acetate (EtOAc), distilled water (dH$_2$O), and butanol (BuOH).

As can be seen in FIG. 4, the hexane fraction showed a strong effect of activating Nurr1 protein, and 1 ppm of the hexane fraction increased the activity of Nurr1 protein to 380%.

Example 7

Effects of Active Ingredients genkwanine N and yuanhuacine

According to a method similar to the method described in Example 3, the concentration dependences of the effects of genkwanine N and yuanhuacine on the activity of Nurr1 protein were analyzed, and the results of the analysis are shown in FIG. 5.

As can be seen in FIG. 5, both the genkwanine N and yuanhuacine compounds showed an activity higher than 300% at 0.3 ppm. Particularly, these compounds increased the activity of Nurr1 protein by 60% and 70% even at low nanomolar concentrations of 16 nM and 15 nM (corresponding to 0.01 ppm), respectively.

The invention claimed is:

1. A method for treating Parkinson's disease, the method comprising administering a composition comprising, as an active ingredient, a *Daphne genkwa* extract or a fraction thereof comprising a compound represented by the following formula 1 or 2 to a subject in need thereof:

Formula 1

Formula 2

2. The method of claim 1, wherein the *Daphne genkwa* extract or the fraction thereof comprise any one or more terpenoid compound selected from the group consisting of a genkawnine N represented by the formula 1 and a yuanhuacine represented by the formula 2; or a pharmaceutically acceptable salt thereof.

3. The method of claim 2, wherein the genkwanine N or the yuanhuacine is a compound isolated from the *Daphne genkwa* extract.

4. The method of claim 1, wherein the composition further comprise a pharmaceutically acceptable carrier.

5. The method of claim 1, wherein the extract is an extract obtained by extraction with water, a $C_1$-$C_5$ lower alcohol, or a mixed solvent thereof.

6. The method of claim 1, wherein the fraction is a hexane fraction or an ethyl acetate fraction.

* * * * *